United States Patent
Liang et al.

(10) Patent No.: US 10,201,389 B2
(45) Date of Patent: Feb. 12, 2019

(54) METHOD AND SYSTEM FOR INTERACTIVE GRID PLACEMENT AND MEASUREMENTS FOR LESION REMOVAL

(71) Applicant: EDDA TECHNOLOGY, INC., Princeton, NJ (US)

(72) Inventors: Cheng-Chung Liang, West Windsor, NJ (US); Guo-Qing Wei, Plainsboro, NJ (US); Li Fan, Belle Mead, NJ (US); Xiaolan Zeng, Princeton, NJ (US); Jianzhong Qian, Princeton Junction, NJ (US)

(73) Assignee: EDDA TECHNOLOGY, INC., Princeton, NJ (US)

( * ) Notice: Subject to any disclaimer, the term of this patent is extended or adjusted under 35 U.S.C. 154(b) by 0 days.

(21) Appl. No.: 15/799,026

(22) Filed: Oct. 31, 2017

(65) Prior Publication Data
US 2018/0116726 A1 May 3, 2018

Related U.S. Application Data

(60) Provisional application No. 62/415,276, filed on Oct. 31, 2016.

(51) Int. Cl.
*A61B 34/10* (2016.01)
*A61B 34/00* (2016.01)
(Continued)

(52) U.S. Cl.
CPC ............. *A61B 34/10* (2016.02); *A61B 34/25* (2016.02); *A61B 90/37* (2016.02); *G06F 3/011* (2013.01);
(Continued)

(58) Field of Classification Search
CPC ......... A61B 34/10; A61B 34/25; A61B 90/37; A61B 2090/367; A61B 2034/105;
(Continued)

(56) References Cited

U.S. PATENT DOCUMENTS 8,275,182 B2 9/2012 Badiei et al.
9,058,651 B2 6/2015 Qian et al.
(Continued)

OTHER PUBLICATIONS

International Search Report and Written Opinion dated Feb. 14, 2018 in International Application PCT/IB2017/056798.

*Primary Examiner* — Abhishek Sarma
(74) *Attorney, Agent, or Firm* — Pillsbury Winthrop Shaw Pittman LLP

(57) ABSTRACT

The present disclosure relates to a system and method of providing surgical assistance. The method includes obtaining a 3D space including an organ and a lesion located within the organ. Based on a shape of the organ, a grid is overlaid on a surface of the organ. The lesion is projected at a first location on an overlaid grid. A graphical tool disposed in a first orientation is positioned at the first location in the 3D space, and a plurality of parameter values of the lesion corresponding to the first orientation of the graphical tool are displayed in the 3D space. The graphical tool is manipulated to be disposed in a second orientation at a second location on the overlaid grid, and the plurality of parameter values of the lesion corresponding to the second orientation of the graphical tool are displayed in the 3D space.

28 Claims, 11 Drawing Sheets

(51) Int. Cl.
  *G06F 3/0338*  (2013.01)
  *G06T 19/00*  (2011.01)
  *G06T 19/20*  (2011.01)
  *G06F 3/01*  (2006.01)
  *G06F 3/0481*  (2013.01)
  *A61B 90/00*  (2016.01)
  *A61B 5/20*  (2006.01)

(52) U.S. Cl.
  CPC ........ *G06F 3/0338* (2013.01); *G06F 3/04815* (2013.01); *G06T 19/00* (2013.01); *G06T 19/006* (2013.01); *G06T 19/20* (2013.01); *A61B 5/201* (2013.01); *A61B 2034/105* (2016.02); *A61B 2034/107* (2016.02); *A61B 2090/367* (2016.02); *G06T 2210/41* (2013.01)

(58) Field of Classification Search
  CPC .............. A61B 2034/107; A61B 5/201; G06F 3/04815; G06F 3/011; G06F 3/0338; G06T 19/00; G06T 19/006; G06T 19/20; G06T 2210/41
  See application file for complete search history.

(56) References Cited

U.S. PATENT DOCUMENTS

| | | | |
|---|---|---|---|
| 2008/0225044 A1 | 9/2008 | Huang et al. | |
| 2009/0257630 A1 | 10/2009 | Liang et al. | |
| 2012/0207268 A1* | 8/2012 | Qian | ...................... A61B 6/037 378/4 |

\* cited by examiner

METHOD AND SYSTEM FOR INTERACTIVE GRID PLACEMENT AND MEASUREMENTS FOR LESION REMOVAL

CROSS-REFERENCE TO RELATED APPLICATIONS

The present application claims priority to U.S. Patent Application No. 62/415,276 filed Oct. 31, 2016, which is incorporated herein by reference in its entirety.

BACKGROUND

1. Technical Field

The present teaching generally relates to the field of lesion removal from an organ of a patient. More specifically, the present teaching relates to an automatic and interactive 3D kidney surface grid placement and measurements for planning of kidney lesion removal. The present teaching can be used in pre-surgical planning to enable physicians to determine an approaching route for the lesion removal procedure and an effective range of the treatment.

2. Technical Background

Nephron sparing surgery (NSS), also known as partial nephrectomy, is a form of kidney surgery where only part of the kidney is removed. It is most often performed in the treatment with solid renal lesions. Traditional treatment for kidney cancer is the surgical removal of the entire kidney and some of the surrounding tissues (called a radical nephrectomy). With NSS, only the tumor and tissue immediately surrounding the tumor is removed, leaving behind a still-functioning kidney.

Open partial nephrectomy (OPN) is generally recognized as one of the standards of care for localized renal masses. Potential problems unique to OPN include inadequate surgical margins, hemorrhage, warm ischemia and urine leak. An endophytic tumor is completely surrounded by normal parenchyma and cannot be detected on visual inspection or palpation. A surgeon first identifies the location of lesion projected to the kidney surface viewing from a potential entry direction. Then the surgeon imagines a cylinder shape to slice into the kidney to cut out the lesion. This procedure requires the knowledge of the size of a lesion, the depth from kidney surface to the lesion, the location and direction from kidney surface to the lesion, and vascular structures around the area. Laparoscopic partial nephrectomy (LPN) and Robotic-Assisted LPN are alternative treatments to reduce patient morbidity.

A nephron sparing surgery procedure requires careful planning to locate the best approaching angle and entry point of the surgical tools. Currently, most of the clinical practices use 2D cross-sectional slices from CT to find the potential treatment areas. This is quite inefficient because users cannot intuitively see the full picture and the 3D spatial relationships among the anatomic structures. Instead, they need to mentally visualize the full area and determine how to reach the target area based on their medical training and experiences. There are some general 3D visualization workstations or software packages that let users prepare and visualize some 3D structures. However, none of them are tailored to NSS procedure. Accordingly, there is a requirement to develop a planning tool that overcomes the above stated deficiencies.

SUMMARY

Aspects of the present disclosure provide for a planning tool to enable users to automatically overlay a grid on top of an organ (e.g., kidney) surface and place a graphical tool such as a cylindrical shaped object around a target lesion. Further, aspects of the disclosure provide users to interactively adjust the overlaid grid and the cylinder. Key measurements related to the cylinder with respect to a target lesion are automatically calculated and displayed directly in the same 3D space (i.e., the 3D space where the anatomic structures reside) for immediate reference. In this manner, users can have a full picture detailing the whole 3D space, 3D anatomic structures, and neighboring structures relationships. Thus, a surgeon can intuitively plan the surgery with confidence and accuracy.

As aspect of the present disclosure provides for a method implemented on a computing device having at least one processor, storage, and a communication platform capable of connecting to a network for surgical procedure assistance. The method includes the steps of: obtaining a 3D space including an organ and a lesion located within the organ; generating and overlaying, based on a shape of the organ, a grid on a surface of the organ; projecting the lesion at a first location on an overlaid grid on the surface of the organ; positioning at the first location, a graphical tool in the 3D space, the graphical tool surrounding the lesion and being disposed in a first orientation; displaying in the 3D space, a plurality of parameter values of the lesion corresponding to the first orientation of the graphical tool; manipulating the graphical tool to be disposed in a second orientation at a second location on the overlaid grid; and displaying in the 3D space, the plurality of parameter values of the lesion corresponding to the second orientation of the graphical tool.

One aspect of the present disclosure provides for a system for surgical procedure assistance. The system comprises at least one processor that is configured to: obtain a 3D space including an organ and a lesion located within the organ; generate and overlay, based on a shape of the organ, a grid on a surface of the organ; project the lesion at a first location on an overlaid grid on the surface of the organ; position at the first location, a graphical tool in the 3D space, the graphical tool surrounding the lesion and being disposed in a first orientation; display in the 3D space, a plurality of parameter values of the lesion corresponding to the first orientation of the graphical tool; manipulate the graphical tool to be disposed in a second orientation at a second location on the overlaid grid; and display in the 3D space, the plurality of parameter values of the lesion corresponding to the second orientation of the graphical tool.

By one aspect of the present disclosure is provided a non-transitory machine readable medium having information recorded thereon for surgical procedure assistance, wherein the information, when read by a machine, causes the machine to perform the steps of: obtaining a 3D space including an organ and a lesion located within the organ; generating and overlaying, based on a shape of the organ, a grid on a surface of the organ; projecting the lesion at a first location on an overlaid grid on the surface of the organ; positioning at the first location, a graphical tool in the 3D space, the graphical tool surrounding the lesion and being disposed in a first orientation; displaying in the 3D space, a plurality of parameter values of the lesion corresponding to the first orientation of the graphical tool; manipulating the graphical tool to be disposed in a second orientation at a second location on the overlaid grid; and displaying in the 3D space, the plurality of parameter values of the lesion corresponding to the second orientation of the graphical tool.

An aspect of the present disclosure provides for a method, implemented on a computing device having at least one processor, storage, and a communication platform capable of connecting to a network for generating a grid to be overlaid on a surface of a 3D image of a kidney. The method includes the steps of: obtaining a first cross-sectional contour of the 3D image of the kidney, the cross-sectional contour including a concave section and a convex section; determining a first end-point and a second end-point of the concave section of the cross-sectional contour; computing, based on the first end-point and second end-point, a third point lying on the convex section of the cross-sectional contour; computing, on the convex section of the cross-sectional contour that is disposed near an anterior side of the kidney, a fourth point between the first end-point and the third point; computing an apex point and a bottom point of the kidney; and generating a grid including a plurality of longitudinal and latitudinal curves based on the first end-point, the second end-point, the third point, the fourth point, and the apex and bottom points.

Additional advantages and novel features will be set forth in part in the description which follows, and in part will become apparent to those skilled in the art upon examination of the following and the accompanying drawings or may be learned by production or operation of the examples. The advantages of the present teachings may be realized and attained by practice or use of various aspects of the methodologies, instrumentalities and combinations set forth in the detailed examples discussed below.

BRIEF DESCRIPTION OF THE DRAWINGS

The methods, systems and/or programming described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

Figure 1:
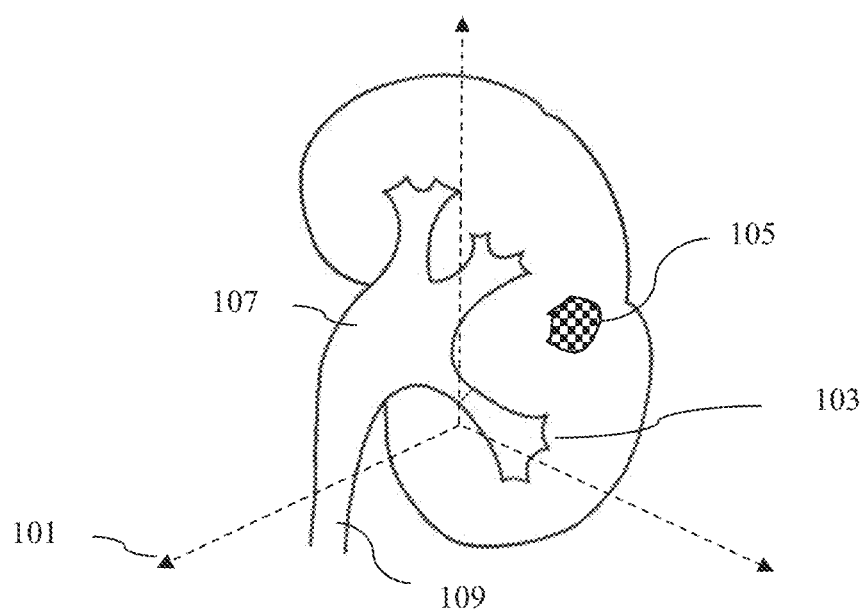
FIG. 1 illustrates an exemplary 3D virtual space for performing Nephron sparing surgery (NSS)

FIG. 1 illustrates an exemplary 3D virtual space 101 for performing Nephron sparing surgery (NSS). Some meaningful urological anatomic structures such as kidney 103 and lesions 105 that are already segmented from a scanned medical data can be placed inside the 3D space. Other related structures such as renal pelvis 107, ureter 109, and renal artery may be optionally available. By one embodiment, the virtual 3D scene is displayed on a 2D screen of a computer monitor. It must be appreciated that the interaction or manipulation occurs inside the virtual 3D space based on user's input from a 2D computer mouse or keyboard, which is converted into 3D actions that are applied to the objects inside the 3D virtual space.

Figure 2A:
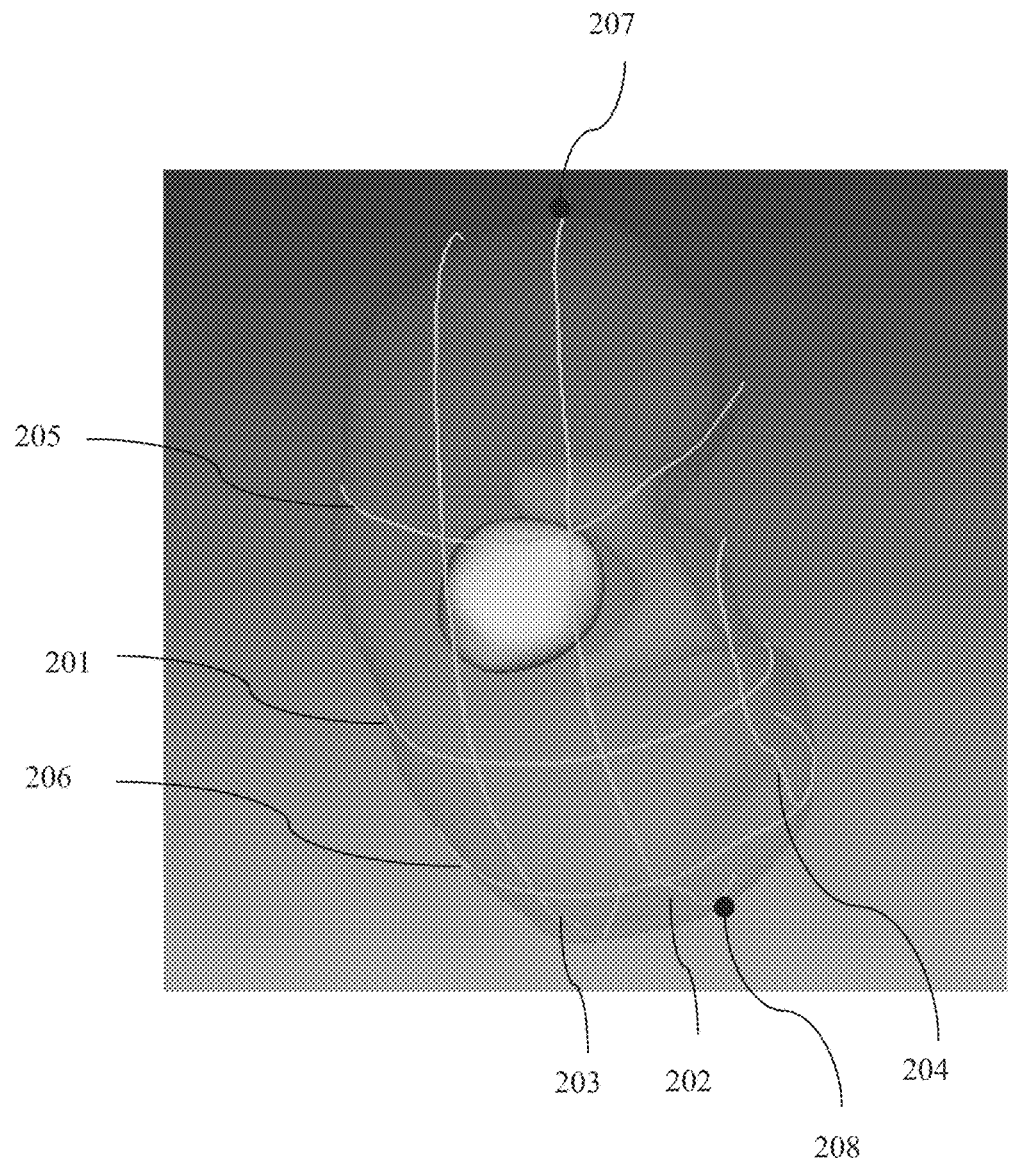
FIG. 2A. depicts an exemplary kidney surface grid that is automatically generated based on a shape of the kidney.
Figure 2B:
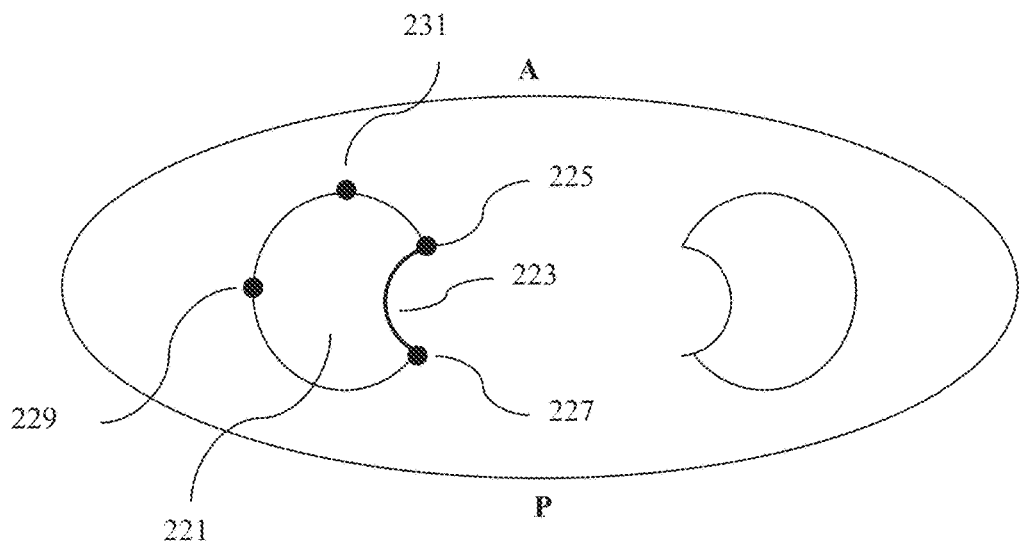
FIG. 2B depicts an exemplary cross section of the kidney.
Figure 2B:
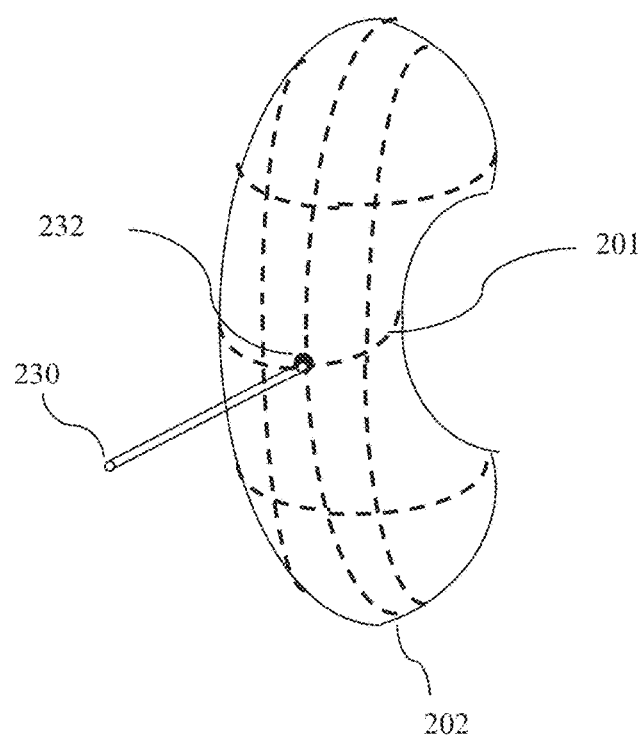

FIG. 2A depicts an exemplary kidney surface grid that is automatically generated based on a shape of the kidney, and FIG. 2B depicts an exemplary cross section of the kidney. A normal kidney has a concave bay on a side closer to the body center. By one embodiment, in order to derive the grid lines, a horizontal cross-sectional contour 221 (as shown in the top figure in FIG. 2B) is obtained through a kidney's geometric center (i.e., the centroid of the kidney). The cross-sectional contour 221 usually passes through the concave bay area and therefore has a concave section 223. The concave section 223 has two end-points, one near patient's anterior side 225, and one near patient's posterior side 227. Based on the two end-points, one can determine the direction to anterior i.e., direction from the posterior ending point to the anterior ending. Further, a farthest point 229, which lies on a convex section of the contour 221, can be determined. The point 229 serves as one end of a middle latitude curve 201 of the grid that is overlaid on the surface of the kidney, while the anterior concave ending point 225 forms the other end of the latitude curve 201. The center point 231 of these two points (i.e., 225 and 229) along the convex section of the contour disposed near the anterior side (depicted as A in top figure of FIG. 2B) is determined as a point through which a center longitude curve 202 needs to pass through.

By one embodiment of the present disclosure, the central longitude curve 202 is derived from a plane formed by three points: the above stated middle point 231, a top apex point 207, and a bottom apex point 208 of the kidney. The top and bottom apex points 207 and 208 respectively, can be determined by fitting an ellipsoid shape to the kidney shape and projecting two points (that are extreme points of a major axis of the ellipsoid) on the kidney shape. Alternatively, by one embodiment, the top and bottom apex points can be computed by determining the points in the top part of kidney and bottom part of kidney respectively, that are disposed furthest away from the kidney's center. A plane which includes the points 231, 207, and 208 intersects the kidney and forms a contour. Specifically, a partial contour section from top apex 207, through the middle point 231, and to the bottom apex 208 forms the central longitude curve 202.

By one embodiment, two additional longitude curves 203 and 204 (that lie on either side of the main longitude curve 202) are generated by moving the central plane to either side of the middle point (231) of the central latitude curve 201. Note that point 231 is determined as a point that passes through the main longitude curve 202. For a specific kidney shape, the middle point may not provide an equal distance gap. If this is the case, one can adjust the plane location to make the gap approximated equal. The starting and ending points of a side longitude curve are determined as the point that has the shortest distance to the starting and ending points of the central longitude curve, respectively.

Further, by one embodiment of the present disclosure, an upper side latitude curve 205 is formed from a cross-sectional contour of the half way slice between the top apex 207 and middle slice 201. In a similar manner, a lower side latitude curve 206 is formed from a cross-sectional contour of the half way slice between the middle slice 201 and bottom apex 208. The latitude sections on cross-sectional contours are determined by a plane formed by the kidney's center, the center of the cross-sectional contour in the half-way slice, and the far-most point. The section is the section in the anterior part after separated by the plane. The two end points of a latitude section may not be ideal or may be even inside of the two longitude curves. If this is the case, some extension to the respective direction is added to a latitude curve and make its length approximately the length from the central longitude to a side longitude.

Upon the latitudinal and longitudinal curves being generated by the method as described above, the curves are overlaid on top of the kidney surface in the 3D virtual space as shown in FIG. 2A. Doing so provides the physicians the advantageous ability of obtaining some indications of roughly where a target lesion will be located, if the lesion is projected to the kidney surface along a potential operation direction. In other words, by overlaying the grid on the surface of the kidney provides a graphical display as to which grid portions/sections should a surgeon focus on while performing surgery.

By one embodiment, if the automatic generated grid is not satisfactory, the grid can be interactively adjusted to other orientations or placements of the grid curves. As shown in FIG. 2B, the orientations of the whole grid pattern can be changed by placing a graphical handle 230 at the intersection point 232 of the central longitude curve 202 and the middle latitude curve 201. A user can manipulate the handle and position the handle at other desired locations on the kidney surface. The grid is moved accordingly with the graphical handle, and is centered at the newly moved location of the handle. By one embodiment, individual grid curves can also be adjusted by directly grabbing (e.g., via a touch operation of the user), a curve in the 3D virtual space and moving the selected curve along either a vertical or horizontal direction. The moved grid curve can automatically embrace (i.e. conform) to the kidney surface.

Figure 3A:
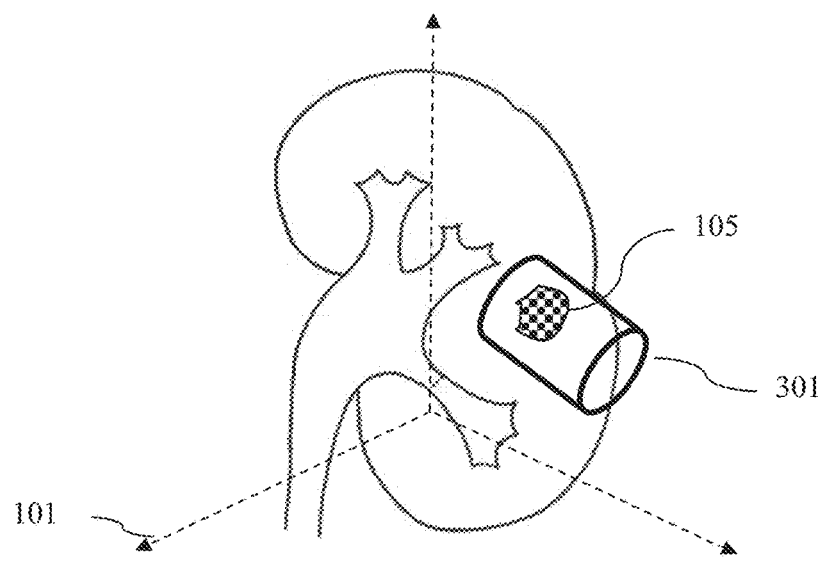
FIG. 3A depicts according to an embodiment, an exemplary graphical tool surrounding a target lesion in the kidney.
Figure 3B:
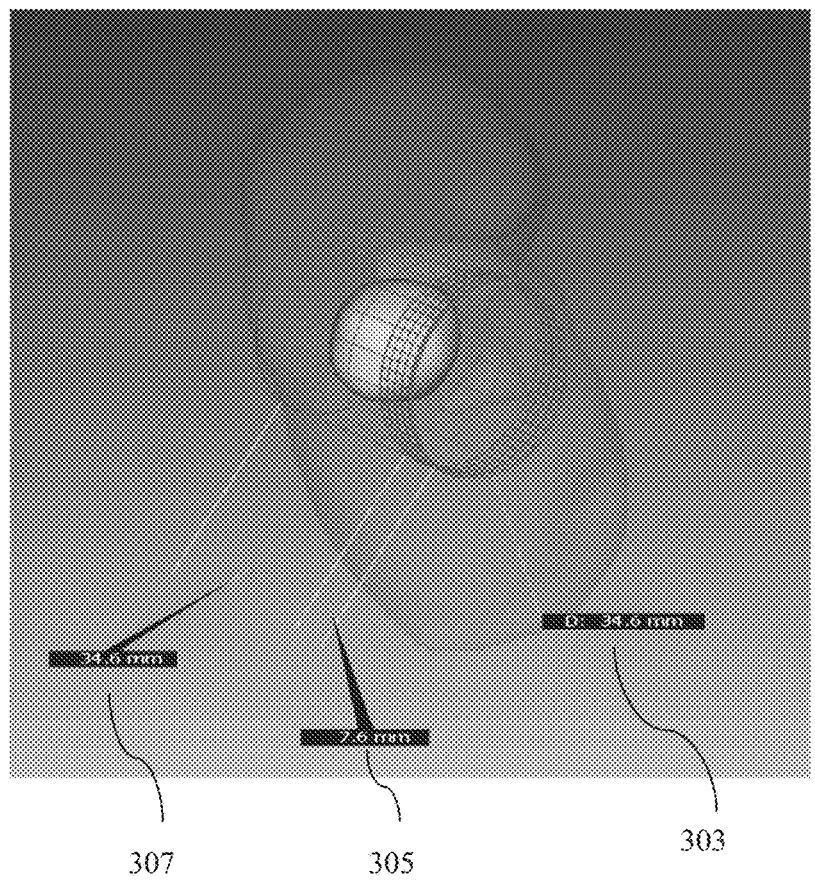
FIG. 3B depicts according to an embodiment, an exemplary graphical tool disposed in a first orientation and a corresponding display of geometric properties of the lesion.

FIG. 3A depicts according to an embodiment, an exemplary graphical tool surrounding a target lesion in the kidney, and FIG. 3B depicts according to an embodiment, an exemplary graphical tool disposed in a first orientation, and a corresponding display of geometric properties of the target lesion.

FIG. 3A depicts a cylinder 301 surrounding a target lesion 105. The initial position and orientation of the cylinder 301 is placed based on the lesion location and oriented toward kidney's forward direction (i.e. a direction from the posterior to the anterior side). A diameter of the cylinder 301 is determined as the maximum diameter of the lesion. With the cylinder 301 protruding through the grid as shown in FIG. 3B, provides physicians with a fair idea as to where the lesion is, if starting from the kidney surface. By one embodiment, the system also provides geometric parameter values of the lesion corresponding to the orientation of the graphical tool (cylinder) such as: (i) physical value of the diameter 303 of the cylinder and/or lesion, (ii) distance 305 from kidney surface to the lesion along the center line, and (iii) distance 307 from the front of the lesion to the back of the lesion. The three geometric parameter values provide physicians with a visual indication as to how deep of a penetration within the kidney (measured from the surface of the kidney) is required to reach the lesion, how much further (i.e. depth of the lesion 307 corresponding to the current orientation of the graphical tool) and how wide (i.e. diameter) to fully sculpt out the whole lesion. It must be appreciated that if the initial orientation and size of the graphical tool (e.g., the cylinder) is not satisfactory to the physician, the system provides interactive means to adjust the orientation, size, and depth of the cylinder as described below.

Figure 4A:
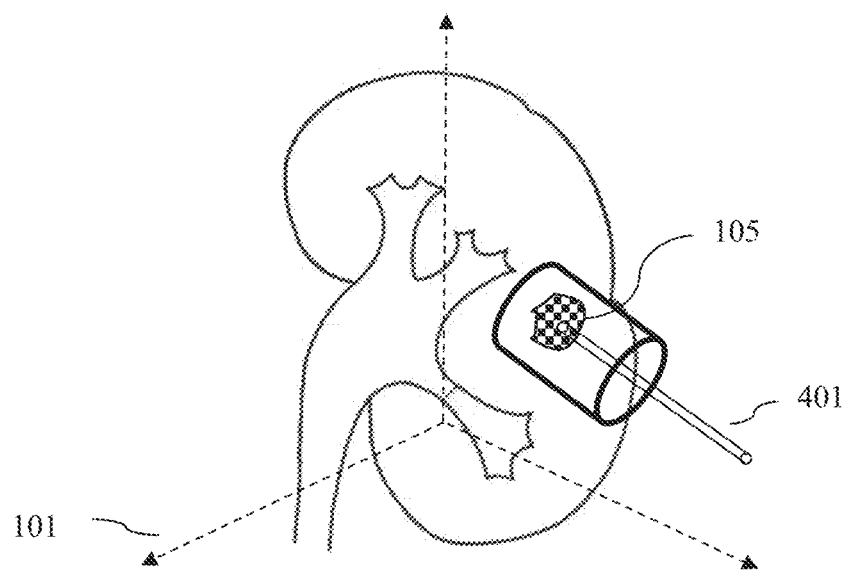
FIG. 4A illustrates according to an embodiment, an exemplary means to adjust an orientation of the graphical tool.
Figure 4A:
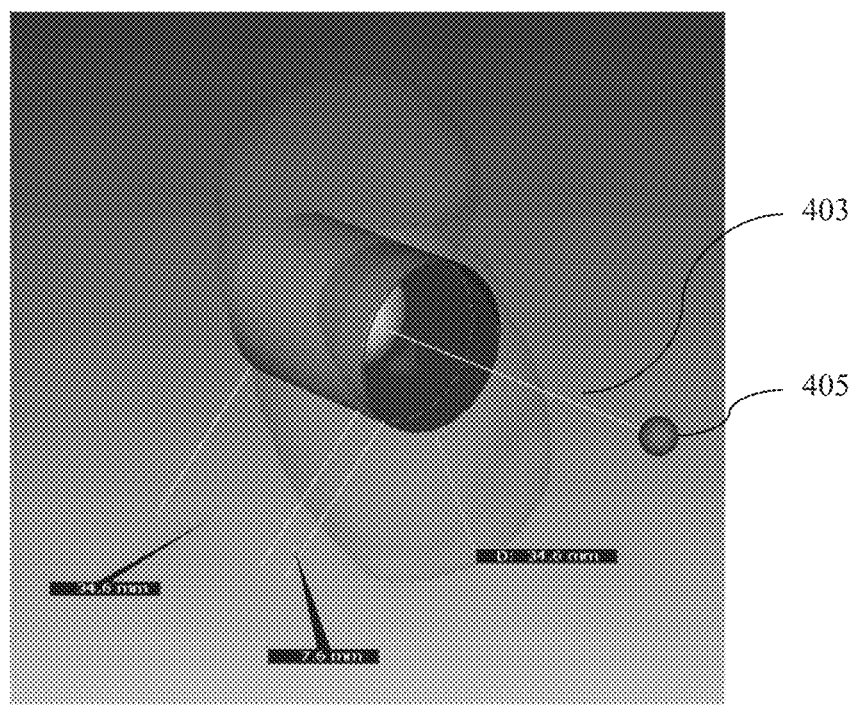
Figure 4B:
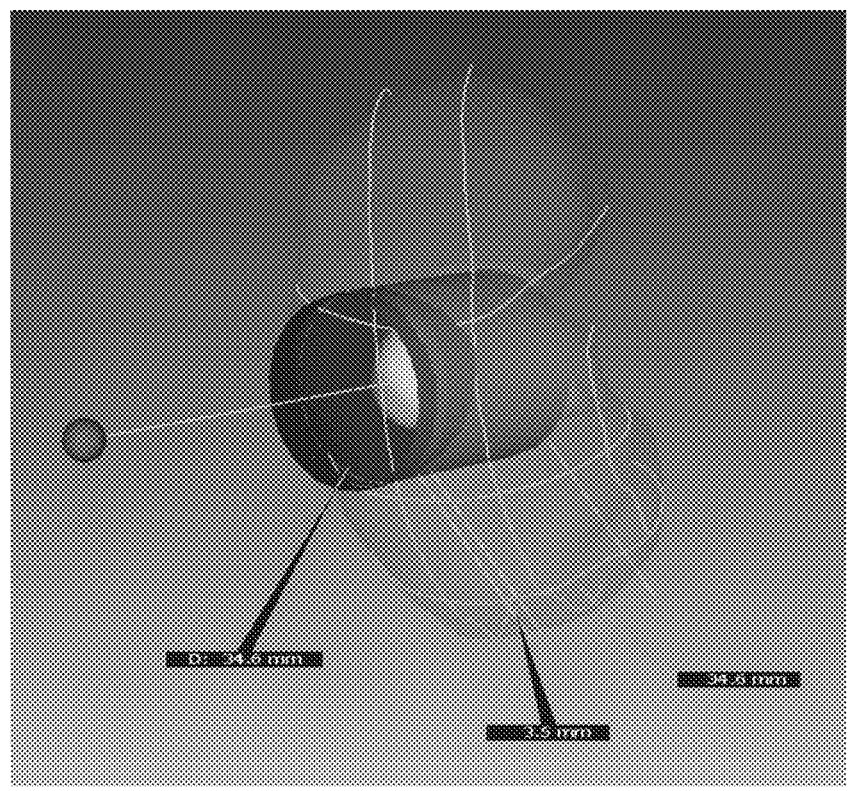
FIG. 4B depicts according to an embodiment, an exemplary graphical tool disposed in a second orientation and a corresponding display of geometric properties of the lesion.

Turning now to FIG. 4A, there is illustrated according to an embodiment of the present disclosure, an exemplary means to adjust an orientation of the graphical tool (e.g., cylinder), whereas FIG. 4B depicts according to an embodiment, the graphical tool being disposed in a second orientation and a corresponding display of geometric properties of the lesion. FIG. 4A shows an exemplary means to adjust the orientation of the cylinder. It must be appreciated that the means is designed to be operated inside the 3D virtual space 101 so that users can gain the best visual feedbacks without leaving the gaze to other places such as operating a slider in a corner of a display screen. By one embodiment, the means to maneuver the graphical tool (cylinder) can be a joystick-like graphical control 401 including a rotating tip that is disposed on the center of the lesion 105, and a control shaft 403 disposed along a central axis of the cylinder. The joystick control includes an end-ball 405 disposed at one end of the control shaft, which can be manipulated to change the orientation of the cylinder. The immediate visual feedback of the new cylinder position provides the geometric properties of the lesion (with respect to the new orientation of the cylinder) to the user as shown in FIG. 4B. Specifically, FIG. 4B depicts a different orientation of the cylinder after users change the orientation using the joystick control and a corresponding display of the three geometric properties of the lesion with respect to the new orientation of the cylinder.

Figure 5:
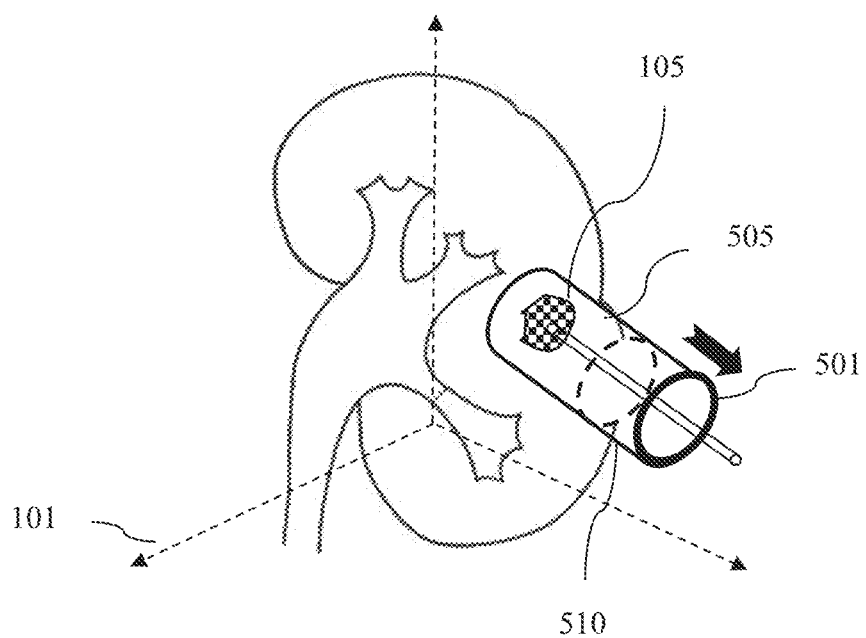
FIG. 5 depicts an exemplary means to adjust a depth of the graphical tool directly within the 3D virtual space.
Figure 6:
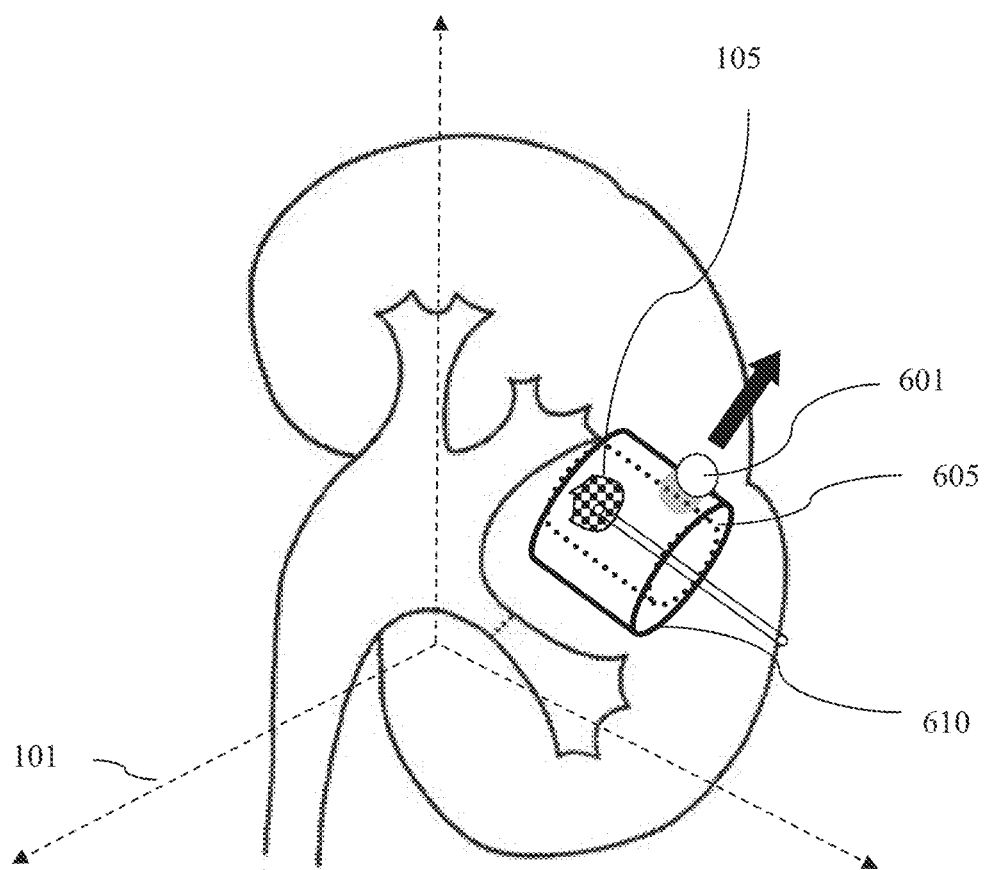
FIG. 6 depicts an exemplary means to adjust a radius (or size) of the graphical tool in the 3D virtual space.

FIG. 5 shows an exemplary means to adjust a depth of the cylinder directly within the 3D virtual space 101. Users can grab either the top edge 501 or the bottom edge of the cylinder 505 and perform a drag operation to change the height of the cylinder to a different one 510. By one embodiment, once the height of the cylinder is changed, the length of the cylinder can also be displayed on the screen for reference purposes. FIG. 6 depicts an exemplary means to adjust a radius (or size) of the cylinder in the 3D virtual space 101. Users can grab (via a touch operation) a graphical control 601 attached to the cylinder 605 and further perform a drag operation in order to expand or shrink the cylinder radius to a new size 610. The diameter value of the cylinder can be updated and displayed accordingly.

Figure 7:
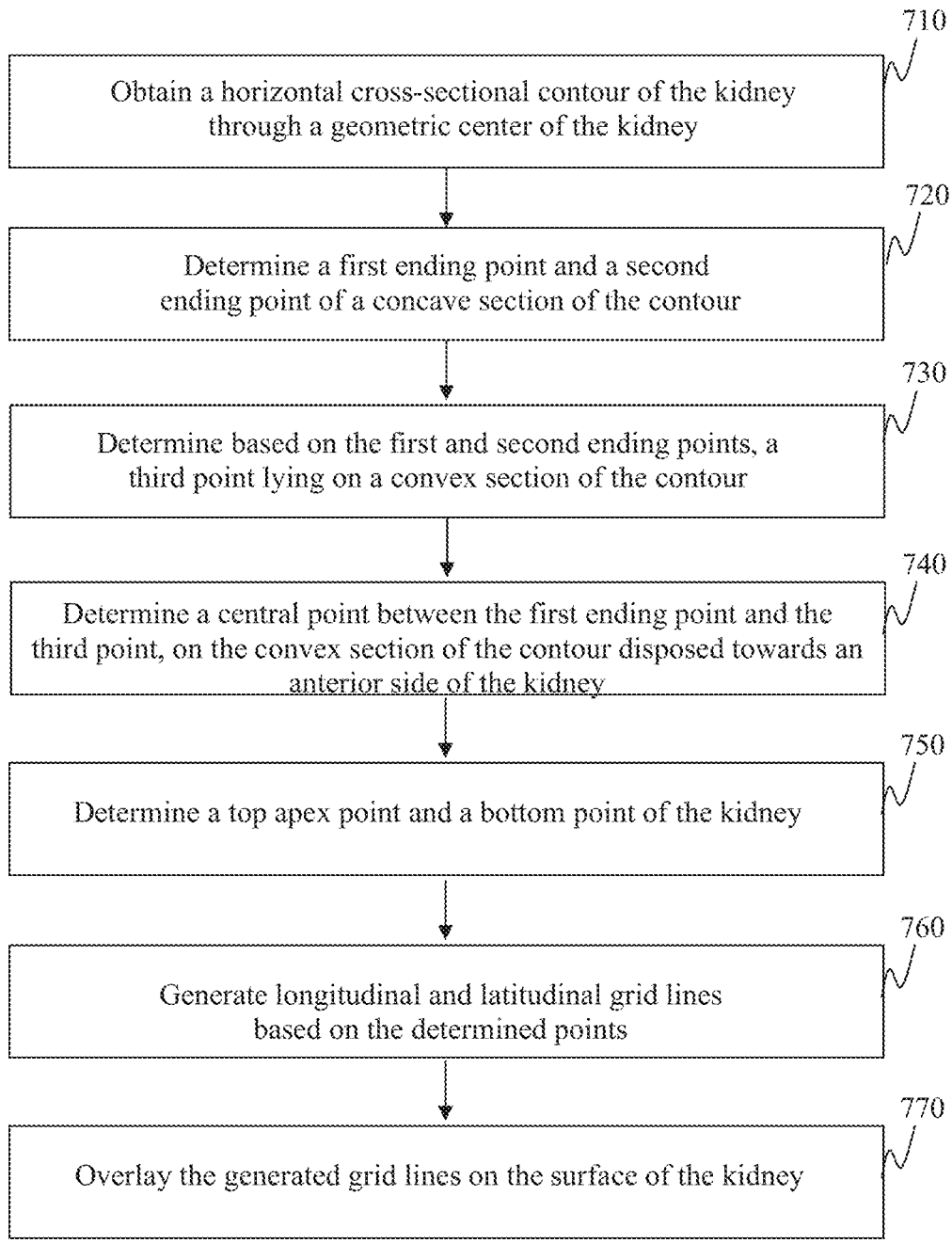
FIG. 7 depicts an exemplary flowchart outlining the steps performed to generate the grid overlaid on the kidney surface.

FIG. 7 depicts an exemplary flowchart outlining the steps performed to generate the grid to be overlaid on the kidney surface. The process commences in step 710, wherein a horizontal cross-sectional contour of the kidney through a geometric center of the kidney is obtained.

In step 720, the process determines a first ending point and a second ending point of a concave section of the cross-sectional contour. As shown in FIG. 2B, the first end-point is disposed at an anterior side of the kidney, and the second end-point is disposed at a posterior side of the kidney.

Further, in step 730, the process determines based on the first and second end-points, a third point lying on a convex section of the contour. The third point is determined to be the point on the convex section of the cross-sectional contour that is disposed furthest away from the first and second end-points that are determined in step 720.

The process further proceeds to step 740, wherein a central point between the first end-point and the third point, on the convex section of the contour disposed towards the anterior side of the kidney is determined. Further, in step 750, a top apex point and a bottom point of the kidney are determined. Note that the apex point and the bottom point can be determined by anyone technique as previously described.

Thereafter, the process proceeds to step 760, wherein a plurality of longitudinal and latitudinal grid lines (curves), based on the above determined points are generated. Specifically, referring back to FIG. 2B, the main latitude curve 201 is determined by the end-point of the concave section of the cross-sectional contour disposed near the kidney's anterior side, and the point (229) that is disposed on the convex section of the cross-sectional contour that is furthest away from the end-points of the concave section of the cross-sectional contour. The main longitudinal curve 202 is determined based on the top-apex point of the kidney, the bottom point of the kidney and the point (231) that lies midway between points 225 and 229 on the convex section of the cross-section contour disposed near the anterior side of the kidney. Further, as stated previously, in addition to the main longitudinal and latitudinal curves, additional longitudinal and latitudinal curves can be generated as described previously. By one embodiment, the plurality of longitudinal and latitudinal grid lines includes three latitudinal curves and three longitudinal curves. Upon generating the plurality of longitudinal and latitudinal grid curves included in the grid, in step 770 of the process, the grid is overlaid on the surface of the kidney.

Figure 8:
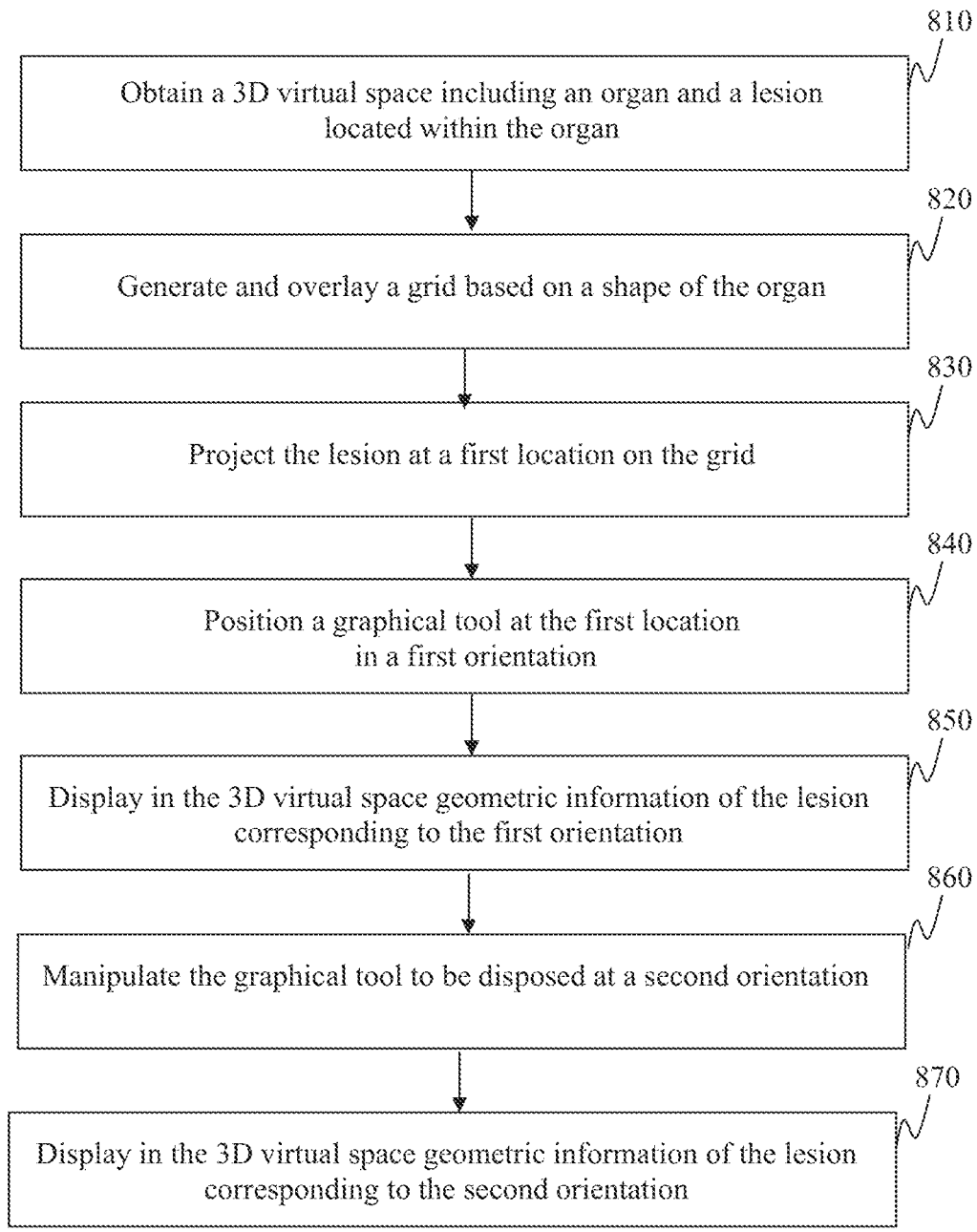
FIG. 8 depicts an exemplary flowchart illustrating the steps performed to provide surgical assistance.

FIG. 8 depicts an exemplary flowchart illustrating the steps performed to provide surgical assistance. The process commences in step 810, wherein a 3D virtual space including an organ (e.g. kidney) and a lesion located within the organ is obtained. Further, the process in step 820 generates and overlays a grid (including a plurality of longitudinal and latitudinal curves) on the surface of the organ. By one embodiment, the grid can be generated and overlaid by the process as described with reference to FIG. 7.

The process of FIG. 8 further proceeds to step 830, wherein the lesion is projected at a first position on grid overlaid on the surface of the organ. Further, in step 840, a graphical tool is positioned at the first location. For instance, a graphical tool such as the cylinder as depicted in FIG. 3A is positioned to surround the lesion in a first orientation.

The process then moves to step 850 wherein geometric information of the lesion corresponding to the first orientation of the graphical tool is displayed in the 3D space. As described previously, the geometric information of the lesion may include (i) physical value of the diameter 303 of the cylinder and/or lesion, (ii) distance 305 from the kidney surface to the lesion along the center line, and (iii) distance 307 from the front of the lesion to the back of the lesion.

Further, in step 860 the graphical tool can be manipulated to be disposed in a second orientation, at a second location on the surface of the organ. By one embodiment, the graphical tool can be manipulated by techniques as described previously with reference to FIG. 4A. By enabling the manipulation of the graphical tool provides the advantageous ability to assist a surgeon in determining a specific route and a depth at which a surgical instrument is to be inserted within the kidney in order to extract the lesion. For instance, by one embodiment, the manipulation may enable the surgeon to determine features such as regions of the organ that are obstructed by bones, major vessels etc, location of other vital organs disposed near the region of operation, a distance of the operating tool to other vital organs and the like. The manipulation may also enable the surgeon to determine surgical tool limitations such as a length constraint of the tool, a size constraint of the tool and the like.

The process upon manipulating the graphical tool, in step 870 displays in the 3D virtual space, geometric information of the lesion corresponding to the second orientation of the graphical tool. It must be appreciated that the steps as depicted in FIG. 8 are in no manner limiting the scope of the present disclosure. Specifically, the steps as depicted in FIG. 8 may be executed along with an operation of another surgical tool. For instance, the graphical tool (e.g., cylinder) can also be incorporated with a virtual ultrasound laparoscopic probe by displaying both the cylinder and the virtual probe in the same 3D virtual space. The ultrasound laparoscopic probe can display the lesion location through a simulated ultrasound scan and thus help determine the lesion location for the cylinder tool.

To implement various embodiments and their functionalities as described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to perform the features as described herein. A computer with user interface elements may be used to implement a personal computer (PC) or other type of work station or terminal device, although a computer may also act as a server if appropriately programmed It is believed that those skilled in the art are familiar with the structure, programming and general operation of such computer equipment and as a result the drawings should be self-explanatory.

Figure 9:
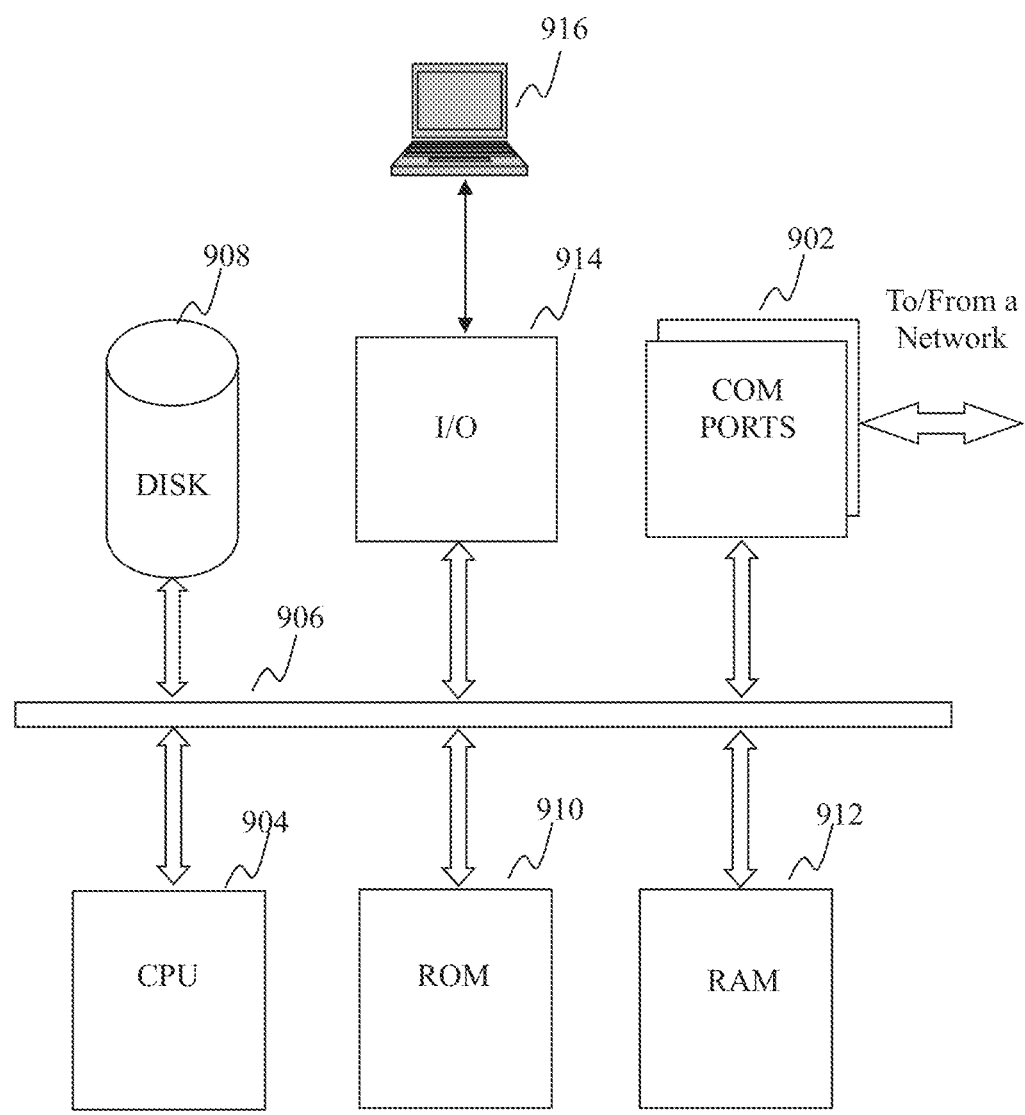
FIG. 9 depicts the architecture of a computer which can be used to implement a specialized system incorporating the present teaching.

FIG. 9 depicts the architecture of a computing device which can be used to realize a specialized system implementing the present teaching. Such a specialized system incorporating the present teaching has a functional block diagram illustration of a hardware platform which includes user interface elements. The computer may be a general purpose computer or a special purpose computer. Both can be used to implement a specialized system for the present teaching. This computer 900 may be used to implement any component of the surgical procedure assistance, as described herein. For example, the features of the present disclosure as described herein may be implemented on a computer such as computer 900, via its hardware, software program, firmware, or a combination thereof. Although only one such computer is shown, for convenience, the computer functions relating to the above described embodiments may be implemented in a distributed fashion on a number of similar platforms, to distribute the processing load.

The computer 900, for example, includes COM ports 902 connected to and from a network connected thereto to facilitate data communications. The computer 900 also includes a central processing unit (CPU) 904, in the form of one or more processors, for executing program instructions. The exemplary computer platform includes an internal communication bus 906, program storage and data storage of different forms, e.g., disk 908, read only memory (ROM) 910, or random access memory (RAM) 912, for various data files to be processed and/or communicated by the computer, as well as possibly program instructions to be executed by the CPU 904. The computer 900 also includes an I/O component 914, supporting input/output flows between the computer and other components therein such as user interface elements 916. The computer 900 may also receive programming and data via network communications.

Hence, aspects of the methods and/or other processes, as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another, for example, from a management server or host computer of a search engine operator into the hardware platform(s) of a computing environment or other system implementing a computing environment or similar functionalities in connection with user interest inference. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine-readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a physical processor for execution.

Those skilled in the art will recognize that the present teachings are amenable to a variety of modifications and/or enhancements. For example, although the implementation of various components described above may be embodied in a hardware device, it may also be implemented as a software only solution—e.g., an installation on an existing server. In addition, the surgical assistance techniques as disclosed herein may be implemented as a firmware, firmware/software combination, firmware/hardware combination, or a hardware/firmware/software combination.

While the foregoing has described what are considered to constitute the present teachings and/or other examples, it is understood that various modifications may be made thereto and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

We claim:

1. A method, implemented on a computing device having at least one processor, storage, and a communication platform capable of connecting to a network for surgical procedure assistance, the method comprising:
    obtaining a 3D space including an organ and a lesion located within the organ;
    generating and overlaying, based on a shape of the organ, a grid on a surface of the organ;
    projecting the lesion at a first location on an overlaid grid on the surface of the organ;
    positioning at the first location, a graphical tool in the 3D space, the graphical tool surrounding the lesion and being disposed in a first orientation;
    displaying in the 3D space, a plurality of parameter values of the lesion corresponding to the first orientation of the graphical tool;
    manipulating the graphical tool to be disposed in a second orientation at a second location on the overlaid grid; and
    displaying in the 3D space, the plurality of parameter values of the lesion corresponding to the second orientation of the graphical tool.

2. The method of claim 1, wherein the organ is a kidney, the graphical tool is a cylinder, and the grid includes a plurality of longitudinal and latitudinal curves.

3. The method of claim 1, wherein the step of generating further comprising:
    obtaining a cross-sectional contour of the organ through a geometric center of the organ, the cross-sectional contour including a concave section and a convex section.

4. The method of claim 3, further comprising:
    determining a first end-point and a second end-point of the concave section of the cross-sectional contour; and computing, based on the first end-point and second end-point, a third point lying on the convex section of the cross-sectional contour.

5. The method of claim 4, further comprising:
computing, on the convex section of the cross-sectional contour that is disposed near an anterior side of the organ, a fourth point between the first end-point and the third point; and
computing an apex point and a bottom point of the organ.

6. The method of claim 5, further comprising:
generating the grid including a plurality of longitudinal and latitudinal curves based on the first end-point, the second end-point, the third point, the fourth point, and the apex and bottom points.

7. The method of claim 1, wherein the plurality of parameter values of the lesion include a diameter of the lesion, a thickness of the lesion, and a distance of the lesion to the surface of the organ.

8. The method of claim 1, wherein the graphical tool is manipulated via a joystick including a shaft disposed along an axis of the graphical tool, the shaft including a tip at one end and a ball at another end, and wherein the tip is disposed at a center of the lesion, and the ball being movable based on a user input.

9. The method of claim 2, wherein a diameter of the cylinder is determined based on a diameter of the lesion, a length and the diameter of the cylinder being adjustable based on a user input.

10. The method of claim 1, further comprising:
adjusting a graphical handle to determine an alignment of the grid, the graphical handle being displayed at a point where a main latitudinal axis and a main longitudinal axis of the grid intersect.

11. A system for surgical procedure assistance, comprising:
at least one processor configured to:
obtain a 3D space including an organ and a lesion located within the organ;
generate and overlay, based on a shape of the organ, a grid on a surface of the organ;
project the lesion at a first location on an overlaid grid on the surface of the organ;
position at the first location, a graphical tool in the 3D space, the graphical tool surrounding the lesion and being disposed in a first orientation;
display in the 3D space, a plurality of parameter values of the lesion corresponding to the first orientation of the graphical tool;
manipulate the graphical tool to be disposed in a second orientation at a second location on the overlaid grid; and
display in the 3D space, the plurality of parameter values of the lesion corresponding to the second orientation of the graphical tool.

12. The system of claim 11, wherein the organ is a kidney, the graphical tool is a cylinder, and the grid includes a plurality of longitudinal and latitudinal curves.

13. The system of claim 11, wherein the at least one processor is further configured to:
obtain a cross-sectional contour of the organ through a geometric center of the organ, the cross-sectional contour including a concave section and a convex section.

14. The system of claim 13, where in the at least one processor is further configured to:
determine a first end-point and a second end-point of the concave section of the cross-sectional contour; and
compute, based on the first end-point and second end-point, a third point lying on the convex section of the cross-sectional contour.

15. The system of claim 14, where in the at least one processor is further configured to:
compute, on the convex section of the cross-sectional contour that is disposed near an anterior side of the organ, a fourth point between the first end-point and the third point; and
compute an apex point and a bottom point of the organ.

16. The system of claim 11, wherein the plurality of parameter values of the lesion include a diameter of the lesion, a thickness of the lesion, and a distance of the lesion to the surface of the organ.

17. The system of claim 11, wherein the graphical tool is manipulated via a joystick including a shaft disposed along an axis of the graphical tool, the shaft including a tip at one end and a ball at another end, and wherein the tip is disposed at a center of the lesion, and the ball being movable based on a user input.

18. The system of claim 12, wherein a diameter of the cylinder is determined based on a diameter of the lesion, a length and the diameter of the cylinder being adjustable based on a user input.

19. A non-transitory machine readable medium having information recorded thereon for surgical procedure assistance, wherein the information, when read by a machine, causes the machine to perform the steps of:
obtaining a 3D space including an organ and a lesion located within the organ;
generating and overlaying, based on a shape of the organ, a grid on a surface of the organ;
projecting the lesion at a first location on an overlaid grid on the surface of the organ;
positioning at the first location, a graphical tool in the 3D space, the graphical tool surrounding the lesion and being disposed in a first orientation;
displaying in the 3D space, a plurality of parameter values of the lesion corresponding to the first orientation of the graphical tool;
manipulating the graphical tool to be disposed in a second orientation at a second location on the overlaid grid; and
displaying in the 3D space, the plurality of parameter values of the lesion corresponding to the second orientation of the graphical tool.

20. A method, implemented on a computing device having at least one processor, storage, and a communication platform capable of connecting to a network for generating a grid to be overlaid on a surface of a 3D image of a kidney, the method comprising:
obtaining a first cross-sectional contour of the 3D image of the kidney, the cross-sectional contour including a concave section and a convex section;
determining a first end-point and a second end-point of the concave section of the cross-sectional contour;
computing, based on the first end-point and second end-point, a third point lying on the convex section of the cross-sectional contour;
computing, on the convex section of the cross-sectional contour that is disposed near an anterior side of the kidney, a fourth point between the first end-point and the third point;
computing an apex point and a bottom point of the kidney; and
generating a grid including a plurality of longitudinal and latitudinal curves based on the first end-point, the second end-point, the third point, the fourth point, and the apex and bottom points.

21. The method of claim 20, wherein the cross-sectional contour is obtained through a geometric center of the kidney.

22. The method of claim 20, wherein the third point is disposed furthest away from the first end-point and the second end-point.

23. The method of claim 20, wherein the plurality of longitudinal and latitudinal curves include a main longitudinal curve and a main latitudinal curve, the first end-point and the third point forming end points of the main latitudinal curve.

24. The method of claim 23, wherein the main longitudinal curve is defined by the apex point, the bottom point, and the fourth point.

25. The method of claim 20, wherein the step of computing the apex point and the bottom point of the kidney, further comprising:

fitting an ellipsoid shape to the 3D image of the kidney; projecting, on the 3D image of the kidney, a pair of endpoints disposed on a major axis of the ellipsoid shape.

26. The method of claim 20, wherein the plurality of longitudinal and latitudinal curves includes three latitudinal curves and three longitudinal curves.

27. The method of claim 23, wherein the plurality of latitudinal curves includes an upper latitudinal curve and a lower latitudinal curve, the upper latitudinal curve being generated based on a second cross-sectional contour of the kidney, the lower latitudinal curve being generated based on a third cross-sectional contour of the kidney.

28. The method of claim 27, wherein the second cross-sectional contour of the kidney is obtained at a first position on the kidney disposed between the apex of the kidney and the main latitudinal curve, and the third cross-sectional contour of the kidney is obtained at a second position on the kidney disposed between the bottom of the kidney and the main latitudinal curve.

* * * * *